United States Patent
Jeoung et al.

(10) Patent No.: US 10,716,826 B2
(45) Date of Patent: Jul. 21, 2020

(54) COMPOSITIONS FOR OVERCOMING ANTI-CANCER DRUG-RESISTANCE OR COMPOSITIONS FOR ANTI-CANCER ACTIVITY EMPLOYING CAGE-DERIVED PEPTIDES

(71) Applicant: L-Base Co., Ltd., Seoul (KR)

(72) Inventors: Dooil Jeoung, Seoul (KR); Youngmi Kim, Gangwon-do (KR); Hyun-a Kim, Gangwon-do (KR)

(73) Assignee: L-BASE CO., LTD., Seoul (KR)

( * ) Notice: Subject to any disclaimer, the term of this patent is extended or adjusted under 35 U.S.C. 154(b) by 198 days.

(21) Appl. No.: 14/978,256

(22) Filed: Dec. 22, 2015

(65) Prior Publication Data

US 2018/0085422 A1 Mar. 29, 2018

(51) Int. Cl.
| | |
|---|---|
| A61K 38/08 | (2019.01) |
| C07K 14/00 | (2006.01) |
| C07K 7/06 | (2006.01) |
| A61K 39/00 | (2006.01) |

(52) U.S. Cl.
CPC .............. A61K 38/08 (2013.01); C07K 7/06 (2013.01); C07K 14/00 (2013.01); *A61K 39/00* (2013.01)

(58) Field of Classification Search
CPC ............................. A61K 38/08; A61K 39/0011
See application file for complete search history.

(56) References Cited

U.S. PATENT DOCUMENTS 6,013,268 A * 1/2000 Reed ...................... C07K 14/44
424/269.1

FOREIGN PATENT DOCUMENTS

| KR | 10-2013-0030080 A | | 3/2013 | |
| KR | 10-2015-0083195 | * | 7/2017 | ............. A61K 38/08 |

OTHER PUBLICATIONS

Machine Translation of Korean Publication No. 10-2015-0083195, published Jul. 17, 2015.*
Saha et al, 269, 342-354 (Year: 1997).*
Seq_search_results, from SCORE (Year: 2017).*

Cho, B., et al., Identification and Characterization of a Novel Cancer/Testis Antigen Gene CAGE, Biochemical and Biophysical Research Communications, 2002, 292(3):715-726, Elsevier Science, USA.
Cho, B., et al., Promoter hypomethylation of a novel cancer/testis antigen gene CAGE is correlated with its aberrant expression and is seen in premalignant stage of gastric carcinoma, Biochemical and Biophysical Research Communications, 2003, 307:52-63, Elsevier Science, USA.
Shim, H., et al., CAGE, a Novel Cancer/Testis Antigen Gene, Promotes Cell Motility by Activating ERK and p38 MAPK and Downregulating ROS, Molecules and Cells, 2006, 21(3):367-375, KSMCB.
Kim, Y., et al., CAGE, a cancer/testis antigen, induces c-FLIP$_L$ and Snail to enhance cell motility and increase resistance to an anticancer drug, Biotechnology Letters, 2009, 31:945-952, SpringerScience+Business Media B.V.
Kim, Y., et al., The cancer/testis antigen CAGE induces MMP-2 through the activation of NF-κB and AP-1, BMB reports, 2009, 42(11):758-763.
Kim, Y., et al., Cancer/Testis Antigen CAGE Exerts Negative Regulation on p53 Expression though HDAC2 and Confers Resistance to Anti-cancer Drugs, The Journal of Biological Chemistry, Aug. 20, 2010, 285(34):25957-25968, The American Society for Biochemistry and Molecular Biology, Inc., USA.
Shim, E., et al., CAGE displays oncogenic potential and induces cytolytic T lymphocyte activity, Biotechnology Letters, 2006, 28:515-522, Springer.

* cited by examiner

*Primary Examiner* — Sudhakar Katakam
(74) *Attorney, Agent, or Firm* — Vorys, Sater, Seymour & Pease LLP; Min Suhn Koh

(57) ABSTRACT

A pharmaceutical anticancer or anticancer drug-resistance composition for a cancer cell, containing a CAGE-derived peptide, is provided. The pharmaceutical anticancer composition contains an effective ingredient of the CAGE-derived oligopeptide with SEQ TD NO.1 or SEQ ID NO.2 and reduces anticancer drug resistance or exhibits an anticancer effect. The pharmaceutical anticancer composition can be employed for a new anticancer drug with advanced anticancer activity of itself, as well as improving a remedy effect with an anticancer drug because of effectively reducing cancer cells, which are resistive to an anticancer drug, and anticancer drug resistance of cancer tissues. The oligopeptide as the effective ingredient of the pharmaceutical anticancer composition is hardly concerned with immunity reaction because of small molecular weight, different from an antibody, and advantageous in effectively overcoming general anticancer drugs because of selective activity to a cancer cell or a cancer tissue.

4 Claims, 20 Drawing Sheets

Specification includes a Sequence Listing.

Figure 6

| Peptide | Sequence | Inhibition of CAGE-GSK3β interaction | CyclinD1 expression | Phosphorylation of GSK3β^ser9 | Apoptotic effect | Anti-cancer activity (in vitro) | Anti-cancer activity (in vivo) |
|---|---|---|---|---|---|---|---|
| CAGE-pep (269-273) | GTGKT | Yes | Down | No | Yes | Yes | Yes |
| T270A | GAGKT | No | Up | Yes | No | No | N.D |
| T273A | GTGKA | Yes | Down | No | Yes | Yes | N.D |
| K272R | GTG8T | No | Up | Yes | No | No | N.D |
| T270A/K272A | GAGAT | No | Up | Yes | No | No | N.D |
| 269-272 | GTGK | No | Up | Yes | No | No | N.D |

```
                        SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: CAGE-derived peptide

<400> SEQUENCE: 1

Gly Thr Gly Lys Thr
1               5

<210> SEQ ID NO 2
<211> LENGTH: 5
<212> TYPE: PRT
<213> ORGANISM: Artificial Sequence
<220> FEATURE:
<223> OTHER INFORMATION: CAGE-derived peptide

<400> SEQUENCE: 2

Gly Thr Gly Lys Ala
1               5
```

COMPOSITIONS FOR OVERCOMING ANTI-CANCER DRUG-RESISTANCE OR COMPOSITIONS FOR ANTI-CANCER ACTIVITY EMPLOYING CAGE-DERIVED PEPTIDES

TECHNICAL FIELD

The present disclosure relates to a pharmaceutical composition including CAGE-derived peptide for overcoming anticancer drug-resistance or for anticancer activity and more particularly, to a pharmaceutical composition exhibiting anticancer activity or overcoming anticancer drug-resistance of cancer cells by including CAGE-derived oligopeptide of SEQ NO.1 or SEQ ID NO.2 as an effective ingredient

BACKGROUND

Despite of improvement in cancer remedy effects owing to continuous development for early cancer diagnostic methods and new anticancer remedies, cancers are still ranking as the first or second cause of death in Korea. Almost anticancer drugs employed at the present time are generally bound with troubles for cancer therapeutics because they act in chemical remedies, being diversified in pharmacological effects according to cancer types, and cause many adverse reactions due to toxicity. As some anticancer drugs may infiltrate into normal cells, as well as cancer cells damage, to damage functions and activity of the cells, there are a lot of problems that cause adverse reactions such as bone marrow depression, gastrointestinal disturbance, or alopecia, and incur multidrug resistance against anticancer drugs due to long-term chemical remedies. For those reasons, many studies and efforts are actively, progressing to develop innovative anticancer drugs capable of overcoming such serious problems of conventional agents.

Since the first report of 1990s about that cancer patients were able to wake up immunities for their own antigens (Lloyd et al., 1990, *Proc. Natl. Acad. Sci.*, 87, 5658-5662), several genes encoding tumor antigens were isolated using tumor-specific Cytotoxic T-Lymphocyte (CTL) (Van den Eynde, B. J. et al., 1997, *Curr. Opin. Immunol.*, 9, 684-693). Additionally, serums of cancer patients were used to excavate auto-antigens, which are named Tumor Associated. Antigen (TAA), through reactions with recombinant cIDNA expression libraries which were produced from various kinds of cancer tissues. Among them, cancer/testis antigens, including Melanoma Associated Antigen (MAGE), GAGE, and BAGE, etc., are kinds of antigens encoded by genes which are expressed not in normal tissues except testicular germ cells but in various kinds of different tissue derived tumors.

Cancer/testis antigens are now principally targeted for development of cancer marker proteins and anticancer vaccines. As an example, there has been a report that six among MAGE and its family tumor antigens, i.e., MAGE-1, 2, 3, 4, 6 and 12, were selectively expressed by considerable parts of primary and transitional tumors including melanoma, lung cancer, bladder cancer, and breast cancer.

A cancer/testis antigen CAGE (Cancer Associated Gene) firstly discovered by the present inventors was found as a new cancer/testis antigen, which is intrinsically resident in a serum of a gastric cancer patient, through the SErological analysis of Recombinant cDNA library EXpressing (SEREX) technique with a cDNA expression library produced from gastric-cancer cell strains and testis tissues (Cho B., 2002, *Biochem. Biophys. Res. Commun.*, 295, 715-726).

And, a study for detection of CAGE methylation has analyzed the association between CAGE expression and DNA demethylation rate of CAGE promoter CpG island (Cho. B., 2003, *Biochem. Biophys. Res. Commun.*, 307, 52-63). This result shows the probability of development for new cancer diagnostic methodology through methylation pattern analysis with CAGE.

In regard to those outcomes of studies for CAGE, over-expression of CAGE increased cell transferability and phosphorylation of ERK, p38 MAPK, or FAK increased cell transferability (Shim H, 2006, *Mol Cells*, 21, 367-375); CAGE induced expressions of cFLIP (c-Flice inhibitory protein) and snail from a celastrol-based anticancer drug-resistance rat-melanoma cell strain and increased cell transferability and resistance against an anticancer drug (Kim Y, 2009, *Biotechnol. Lett.*, 31, 945-952); CAGE induced expression of MMP-2 through activity of NF-kB/AP-1 (Kim Y., 2009, *BMB reports*, 42, 758-763); CAGE suppressed expression of p53 through interaction with HDAC2 in a celastrol-based anticancer drug-resistance cell strain (liver cancer SNU387$^R$, melanoma Malme3M$^R$) and thereby allows resistance against an anticancer drug (Kim Y, 2010, *J. Biol, Chem.*, 285, 25957-25968); and peptides derived from CAGE proteins increased activity of cell-toxic T-lymphocytes to exhibit anticancer property (Shim E., 2006, *Biotechnol. Lett.*, 28, 515-522).

In the meantime, the present inventors previously made a patent application disclosing that CAGE induced anticancer drug-resistance which is caused from phosphorylation of Glycogen Synthase Kinase-3 beta (GSK3β) Ser9 residues and accumulation of Cyclin D1 in atoms through the phosphorylation. (Korean Patent Publication No. 10-2013-0030080), Although antibodies toward specific tumor antigens for tumor cells are being in development, antibodies are concerned with immune response and have low infiltration efficiency. Different from antibodies, peptides are regarded as being lightly concerned with immune response and as being advantageous for infiltration into tissues because of their small molecular weight. As peptide-based anticancer drugs toward tumor antigens can selectively act to tumors, they may hardly cause adverse reactions such as damage to normal cells.

The present inventors have reported that CAGE acted as new carcinogen to permit resistance against anticancer drugs, which was found out through the former efforts, and have studied new anticancer peptides targeting cancer/testis antigen CAGE under the research background. As a result, they found that GTGKT(269-273)-based oligopeptides, which correspond to ATP binding regions of CAGE proteins, suppress anticancer drug resistance and tumor generation in an anticancer drug-resistance cell strain, and reached the present disclosure.

PRIORS ART DOCUMENTS

Patents

Patent Document 1: Korean Patent Publication No. 10-2013-0030080

Non-Patents

Non-patent Document 1: Cho B., 2002, *Biochem. Biophys. Res. Commun.*, 295, 715-726

Non-patent Document 2: Cho. B., 2003, *Biochem. Biophys. Res. Commun.*, 307, 52-63

Non-patent Document 3: Shim H., 2006, *Mol Cells*, 21, 367-375

Non-patent Document 4: Kim Y, 2009, *Biotechnol. Lett.*, 31, 945-952

Non-patent Document 5: Kim Y, 2009, *BMB reports*, 42, 758-763

Non-patent Document 6: Kim Y., 2010, *J. Biol, Chem.*, 285, 25957-25968

Non-patent Document 7: Shim E., 2006, *Biotechnol. Lett.*, 28, 515-522

SUMMARY

Aspects of the present disclosure are to address at least the above-mentioned problems and/or disadvantages and to provide at least the advantages described below. Accordingly, an aspect of the present disclosure is to provide a new anticancer drug specifically effective in cancer cells and having high anticancer activity.

Another aspect of the present disclosure is to provide an anticancer adjuvant capable of lessening resistance against an anticancer drug to improve therapeutic effects.

In accordance with an aspect of the present disclosure, a pharmaceutical anticancer composition may include an effective ingredient of an oligopeptide with SEQ ID NO.1 (GTGKT) of amino acid.

In accordance with another aspect of the present disclosure, a pharmaceutical anticancer composition may include an effective ingredient of an oligopeptide with SEQ ID NO.2 (GTGKA) of amino acid.

In accordance with still another aspect of the present disclosure, a pharmaceutical anticancer drug-resistance reducing composition for a cancer cell may include an effective ingredient of an oligopeptide with SEQ ID NO.1 (GTGKT) of amino acid.

In accordance with further still another aspect of the present disclosure, a pharmaceutical anticancer drug-resistance reducing composition for a cancer cell may include an effective ingredient of an oligopeptide with SEQ ID NO.2 (GTGKA) of amino acid.

An oligopeptide according to the present disclosure may exhibit advanced anticancer activity specifically in cell strains of a skin cancer, a liver cancer, and a gastric cancer.

An oligopeptide according to the present disclosure may have improved effects in cancer cells which are resistive specifically to celastrol or taxol.

An oligopeptide according to the present disclosure may be bound with a CAGE protein to hinder the inter-binding between CAGE and GSK3β and thereby to suppress anticancer multidrug resistance of a cancer cell. CAGE (cancer associated gene) is a cancer/testis antigen. Information about amino acid sequences and gene sequences for CAGE is registered as AY039237.1 in the GenBank database. GSK3β (glycogen synthase kinase-3 beta) is registered as GCID: GC03M1119540 in the GeneCards database.

An oligopeptide according to the present disclosure may suppress migration of a CAGE toward atoms to suppress expression of Cyclin D1 due to a CAGE protein.

An oligopeptide according to the present disclosure, as a tumor-specific peptide, may have a function of specific infiltration into a high-CAGE tumor tissue not into a normal tissue.

An oligopeptide according to the present disclosure may suppress tumor generation which is caused from a CAGE.

An oligopeptide according to the present disclosure may be formulated based on formulation standards for usual pharmaceutical materials or for health supplement food by Ministry of Food and Drug Safety An oligopeptide according to the present disclosure may be used by itself or may be used in a form of acid addition salt or metal composite which is permitted by phamaceutical usage, e.g., in a form of salt such as zinc, iron, etc. In more detail, the acid addition salt may be adopted from hydrogen chloride, hydrogen bromide, sulfate, phosphate, maleate, acetate, citrate, benzoate, succinate, malate, and tartalate.

Additionally, it may be preferred for a pharmaceutical anticancer composition according to the present disclosure to be mixed and diluted with a carrier which pharmaceutically, permits the oligopeptide, based on an administration method, an administration pattern, and a therapeutic purpose, in a usual process, or to be loaded in a receptacle-type carrier.

In the case of being used for a dilution, the carrier may be prepared in a formulation such as powder, granules, injections, syrups, solution agents, tablets, suppositories, pessaries, ointments, creams, or aerosols for oral or non-oral administration using one or more selected from a group of brine, buffer, dextrose, water, glycerol, ringer solution, lactose, sucrose, calcium silicate, methyl cellulose, and ethanol. However, the carrier may not be restrictive to those kinds. Hereat, non-oral administration means administration of an effective ingredient through a rectum, a vein, a peritoneum, a muscle, an artery, a scierite, a nasal cavity, or inhalation.

Formulation may be allowable to provide a rapid, continuous, or delayed discharge of active ingredients after additionally administering a filler, an anti-coagulant, a lubricant, a wetting agent, a perfume, an emulsifier, an antiseptic, etc., which are added to the formulation, into a mammal. Although an amount of administration may be controlled according to a condition of a patient, an administration path, and an administration pattern without limitation and may be diversified in various ranges according to symptoms by those skilled in the art, an oligopeptide according to the present disclosure may be continuously or intermittently administered as much as about 1 mg for a body weight of 1 kg a day.

According to embodiments, a pharmaceutical composition of the present disclosure may effectively lessen anticancer drug-resistance of cancer cells or cancer tissues which have resistance against an anticancer drug and may be employed for a new anticancer drug as well as improving therapeutic effects of the anticancer drug.

Additionally, oligopeptide, which acts as an active ingredient of a pharmaceutical composition according to the present disclosure, may suppress immune reaction, because of its small molecular weight, and may easily infiltrate into tissues. The oligopeptide is regarded as being effective in removing adverse reactions of conventional anticancer drugs because it may act selectively to cancer cells or cancer tissues.

BRIEF DESCRIPTION OF THE DRAWINGS

FIG. 6 summarizes apoptotic states and anticancer activities of peptides inducing deletion and mutation of specific amino acid residues of CAGE-derived GTGKT peptides.

DETAILED DESCRIPTION

Figure 1A:
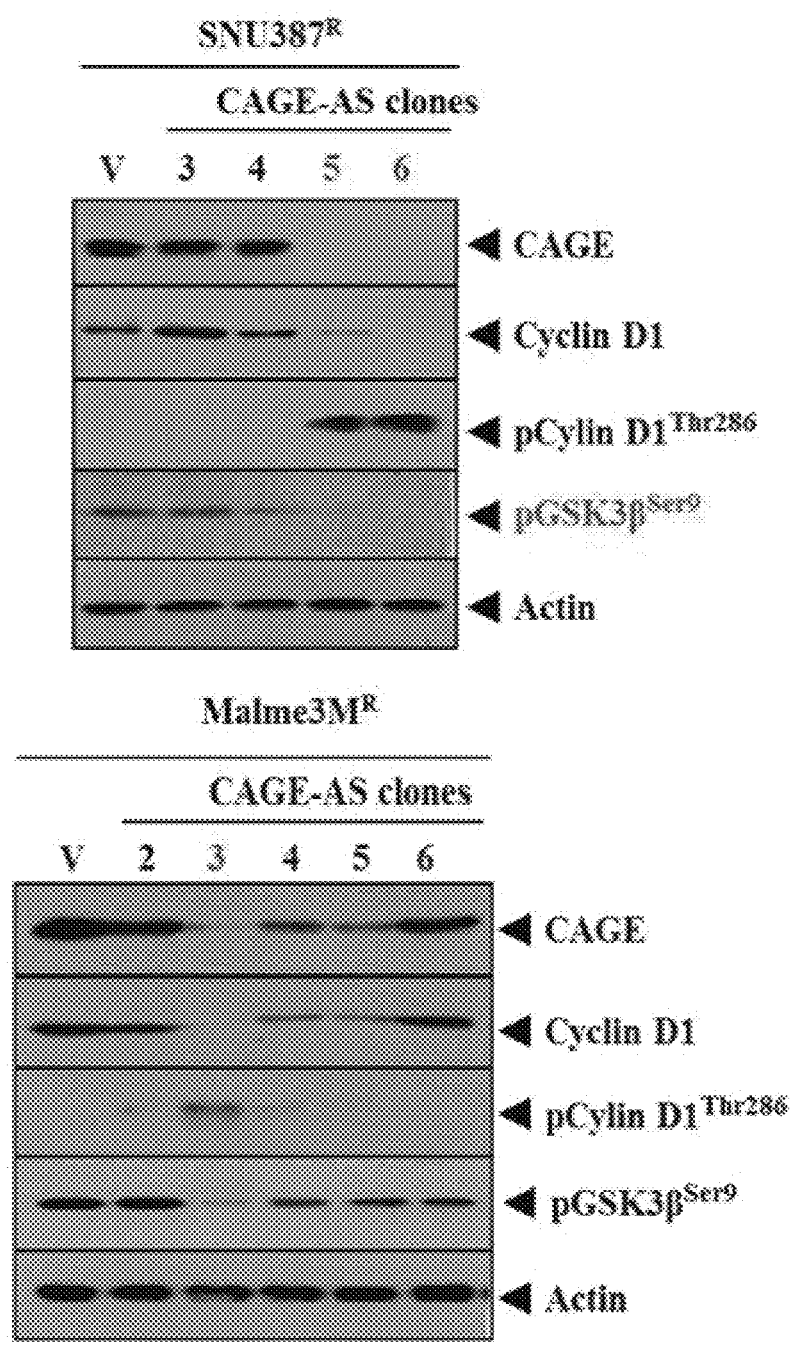
FIG. 1A shows a result of hindering phosphorylation of GSK3β Ser9 residues, dephosphorylation of Cyclin D1 Thr286 residues, and accumulation in the case of stably transfecting antisense CAGE (CAGE-AS clone) into celastrol-based anticancer drug-resistance cell strains of liver cancer and melanoma skin cancer.

Hereinafter, various embodiments of the present disclosure will be described in conjunction with the accompanying drawings. Various embodiments described herein, however, may not be intentionally confined in specific embodiments, but should be construed as including diverse modifications, equivalents, and/or alternatives. With respect to the descriptions of the drawings, like reference numerals refer to like elements.

<Tumor Generation of Cancer/Testis Antigen CAGE>

An affection of CACG causing tumor generation was inspected.

To this end, a liver-cancer cell strain ($SNU387^R$-AS CAGE) and a melanoma cell strain ($Malme3M^R$-AS CAGE) were prepared through a known method (Kim Y, Park D, Kim H, Choi M, Lee H, Lee Y S, Choe J, Kim Y M, Jeong D., 2013, J. Biol. Chem., 288(51), 36502-18), and those cell strains and an immunodeficiency mouse are used to inspect a function of a CAGE and an affection of the CAGE causing tumor generation.

As shown in FIG. 1A, in cell strains in which anti-sense CAGE cDNA was expressed to stably lessen CAGE expression, expression of Cyclin D1 was reduced, phosphorylation (Thr286) of Cyclin D1 was leveled down, and phosphorylation of GSK3β was leveled down. From the results, such reduction of CAGE expression controls a phosphorylation level of Cyclin D1 and GSK3β to adjust an expression level of Cyclin D1.

Figure 1B:
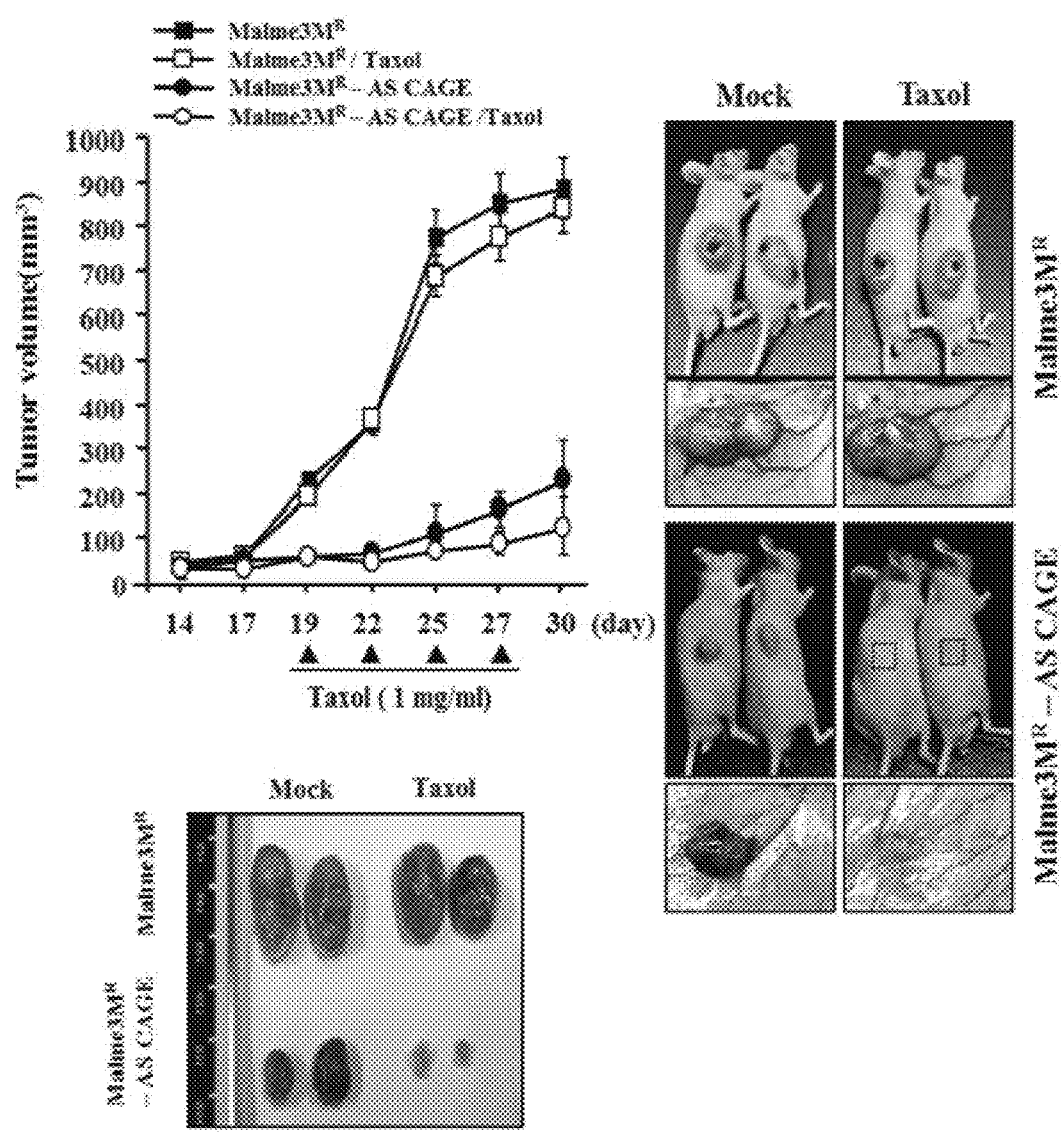
FIG. 1B shows a result of hindering tumor generation and anticancer resistance against Taxol in the case of suppressing expression of CAGE from a melanoma skin-cancer cell strain in an immunodificiency mouse.

A melanoma cell strain ($Malme3M^R$-AS CAGE), which was stably reduced in CAGE expression, of $1\times10^6$ was injected into the side abdomen of a nude mouse. If a tumor grew up to a size enough to be measured, a digital gauge was used to a size of the tumor in a uniform interval and the tumor size was calculated by a known equation (the widest length [the shortest length]$^2\times0.5$). After inducing a tumor in the same manner, taxol was injected into a vein of the mouse's tail for inspection to tumor generation and anticancer drug resistance. Consequently, as shown in FIG. 1B, the reduction of CAGE expression lessened tumor generation which was caused by the Malme3MR cell stain, and increased the sensitivity to taxol.

Figure 2:
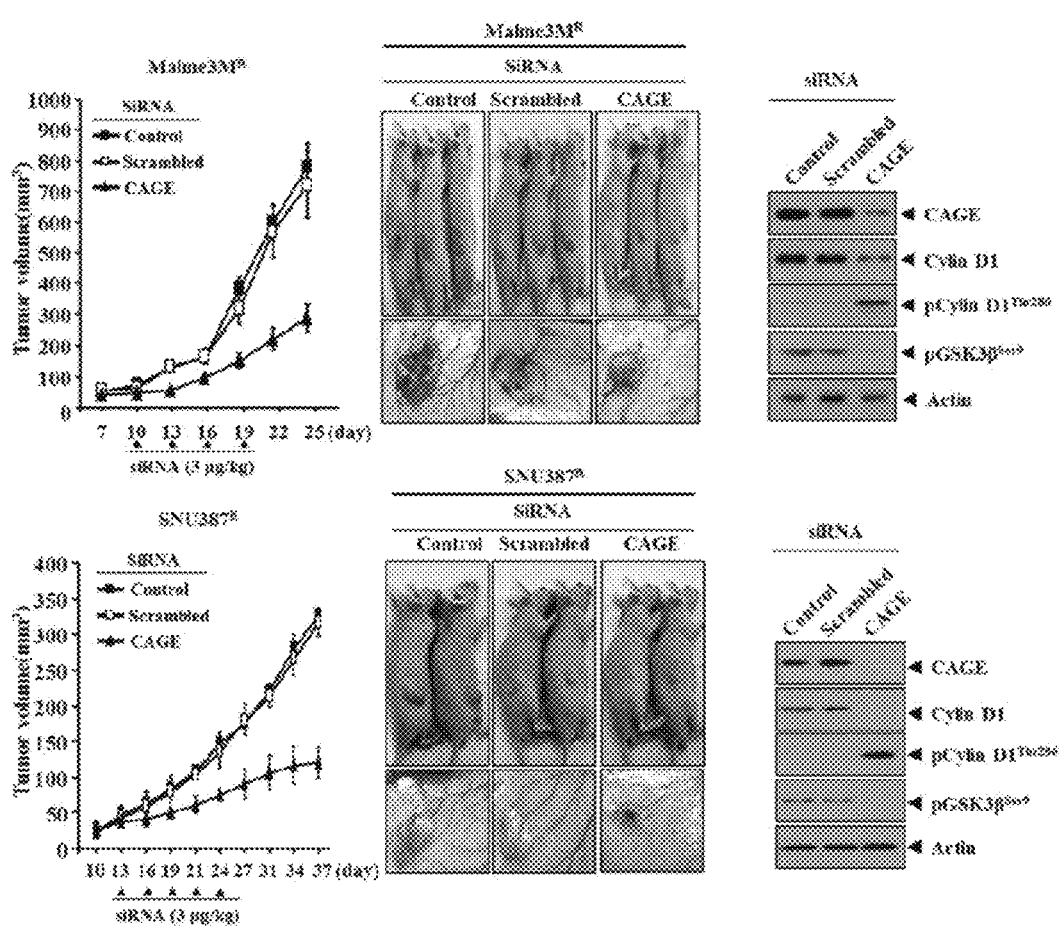
FIG. 2 shows a result that CAGE siRNA reduces a tumor size of celastrol-based anticancer drug-resistance cell strains of liver cancer and melanoma and the Western blot confirms an expression pattern of genes from the tissues.

After inducing a tumor by injecting respective cancer cell strains, siCAGE (3 μg, siRNA to mRNA of CAGE) was injected into a vein of the mouse's tail 4 times in total every 3 μg, days for 2 weeks. Then, to confirm expression of a protein from the tumor tissue, an extracted tumor issue was crashed by liquid nitrogen through a traditional method, reacted with a dissolution buffer and ice for 30 minutes, and next separated through a centrifugal for 15 minutes, and then the upper liquid was collected with a protein sample. Hereinafter, the Western blot was used to confirm patterns of expression and activity of proteins, as shown in FIG. 2.

From the experimental results, it could be seen that protein accumulation of Cyclin D1 was induced by CAGE through dephosphorylation of Cyclin D1 Thr286 residues, phosphorylation of GSK3β Ser9 residues, and tumor generation by over-expression of a drug-resistance cell strain.

<CAGE Activity Suppression by GTGKT-Based Oligopeptide>

Figure 3A:
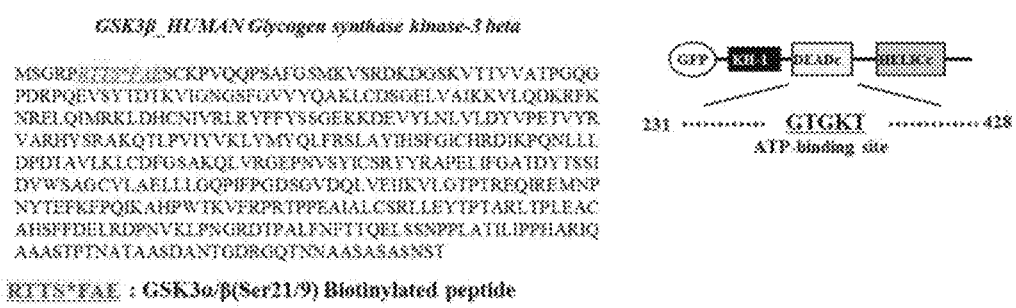
In FIG. 3A, the left panel shows that a peptide RTSSFAE sequence, which includes GSK3β Ser9 residues, is employed for a temperament of a kinase assay which confirms phosphorylation of the GSK3β Ser9 by CAGE, and the right panel shows a GTGKT peptide sequence, which includes ATP-binding sites, among DEADc domains corresponding to amino acid sequences 231~428 of a CAGE protein.

To confirm an affection of CAGE-derived oligopeptide to the interbinding and GSK3β Ser9 phosphorylation of a CAGE, a GTGKT (Sequence No.1) peptide and a specific-residue deleted and mutated peptide based on the GTGKT peptide were prepared and, after collecting proteins by a known method after transfection into respective cell stains, the Western blot and the immunoprecipitation were preformed to inspect an anticancer drug-resistance induction mechanism of the CAGE. GTGKT includes ATP binding sites of CAGE (the right panel of FIG. 3A).

Figure 3B:
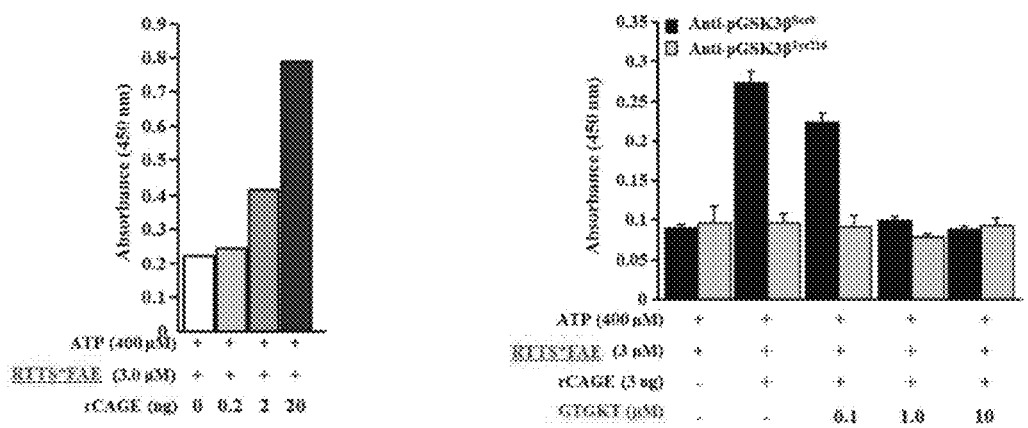
FIG. 3B shows results that an ATP-boding GTGKT peptide specifically hinders phosphorylation of GSK3β Ser9 residues by CAGE: the left panel shows the result of kinase assay that a reassociated CAGE protein phosphorylates the GSK3β Ser9 residues with GSK3β Ser9 specific peptide KTSSFAE; and the right panel shows the GTGKT peptide hinders phosphorylation of GSK3β Ser9 residues by the reassociated CAGE protein.
Figure 4A:
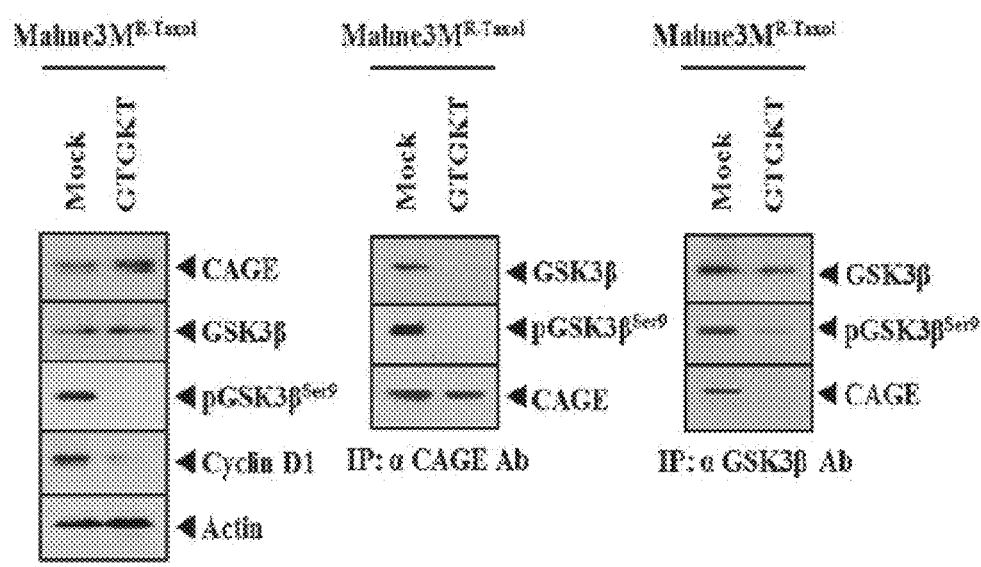
FIG. 4A shows that a CAGE-based GTGKT peptide suppresses phosphorylation of GSK3β Ser9 residues, accumulation of Cyclin D1 proteins, and the inter-binding between CAGE and the phosphorylated GSK3β in a taxol-based anticancer drug-resistance melanoma skin-cancer cell strain.
Figure 4B:
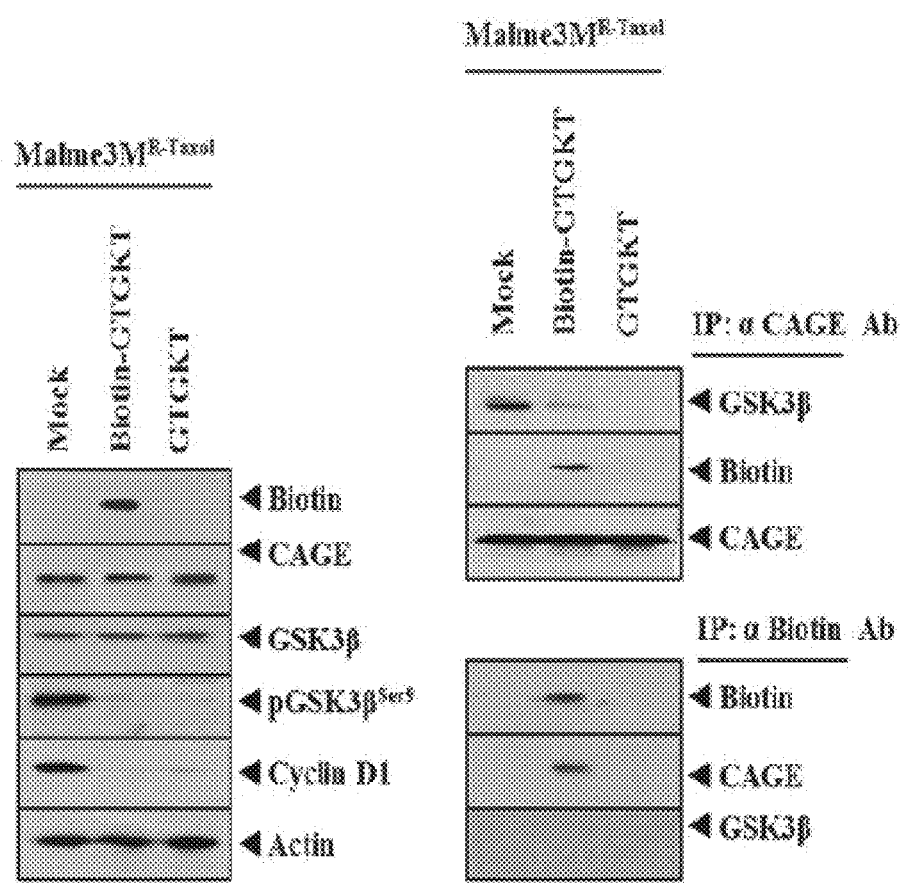
FIG. 4B shows a result that a CAGE-based GTGKT peptide suppresses phosphorylation of GSK3β Ser9 residues, accumulation of Cyclin D1 proteins, and the inter-binding between CAGE and the phosphorylated GSK3β through the boding with the CAGE protein in a taxol-based anticancer drug-resistance melanoma skin-cancer cell strain.

A GSK3β-described peptide RTTSFAE including GSK3β Ser9 residues was prepared for a temperament (the left panel of FIG. 3A) and phosphorylation of the GSK3β Ser9 residues by a reassociated CAGE protein was confirmed through an in vitro kinase assay by using the RTTSFAE peptide as the temperament (the left panel of FIG. 4B). In addition to this, it was confirmed that after treatment with the GTGKT peptide, the GSK3β Ser9 residues were suppressed in phosphorylation due to the reassociated CAGE protein (the right panel of FIG. 3B).

As shown in FIG. 4A, from a result of inspection for affections of GTGKT peptide to a protein expression pattern by CAGE and to phosphorylation, through the Western blot and the immunoprecipitation, in a taxol-resistance melanoma cell strain (Malme3M$^{R\text{-}Taxol}$), it could be seen that GTGKT hindered the CAGE-GSK3β inter-binding to suppress phosphorylation of GSK3β Ser9 residues and protein accumulation of Cyclin D1. Additionally, the same result were shown even in the case of preparing a Biotin-GTGKT peptide (FIG. 4B).

Figure 4C:
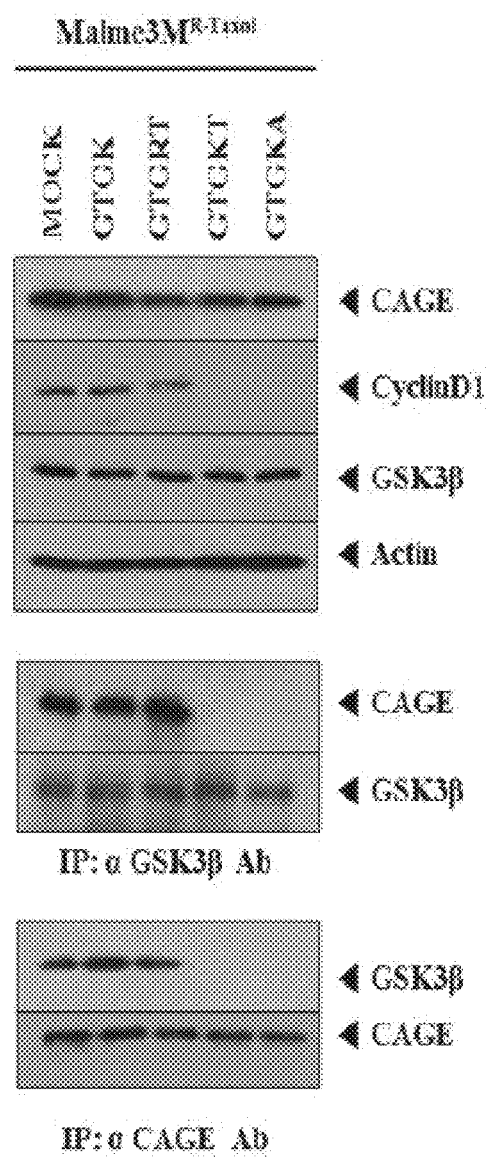
FIG. 4C shows a result that after deletion or mutation of specific amino acid residues of CAGE-derived GTGKT peptide sequence, a GTGKA, in which the 273'rd Thr residue is substituted for Ala, exhibits the same effect with a GTGKT.

To examine residues necessary for anticancer activity of a GTGKT peptide, after preparing a peptide for which the 273'rd Thr residue is deleted (GTGK) or substituted (GTGKA, sequence No. 2) with Ala in CAFE, and preparing a peptide for which the 272'nd Ala residue is substituted (GTGRT) with Arg, the same manner was performed. As a result, it could be seen from FIG. 4C that the GTGKA peptide suppressed the inter-binding between CAGE and GSK3β proteins to control an expression level of Cyclin D1.

Figure 5A:
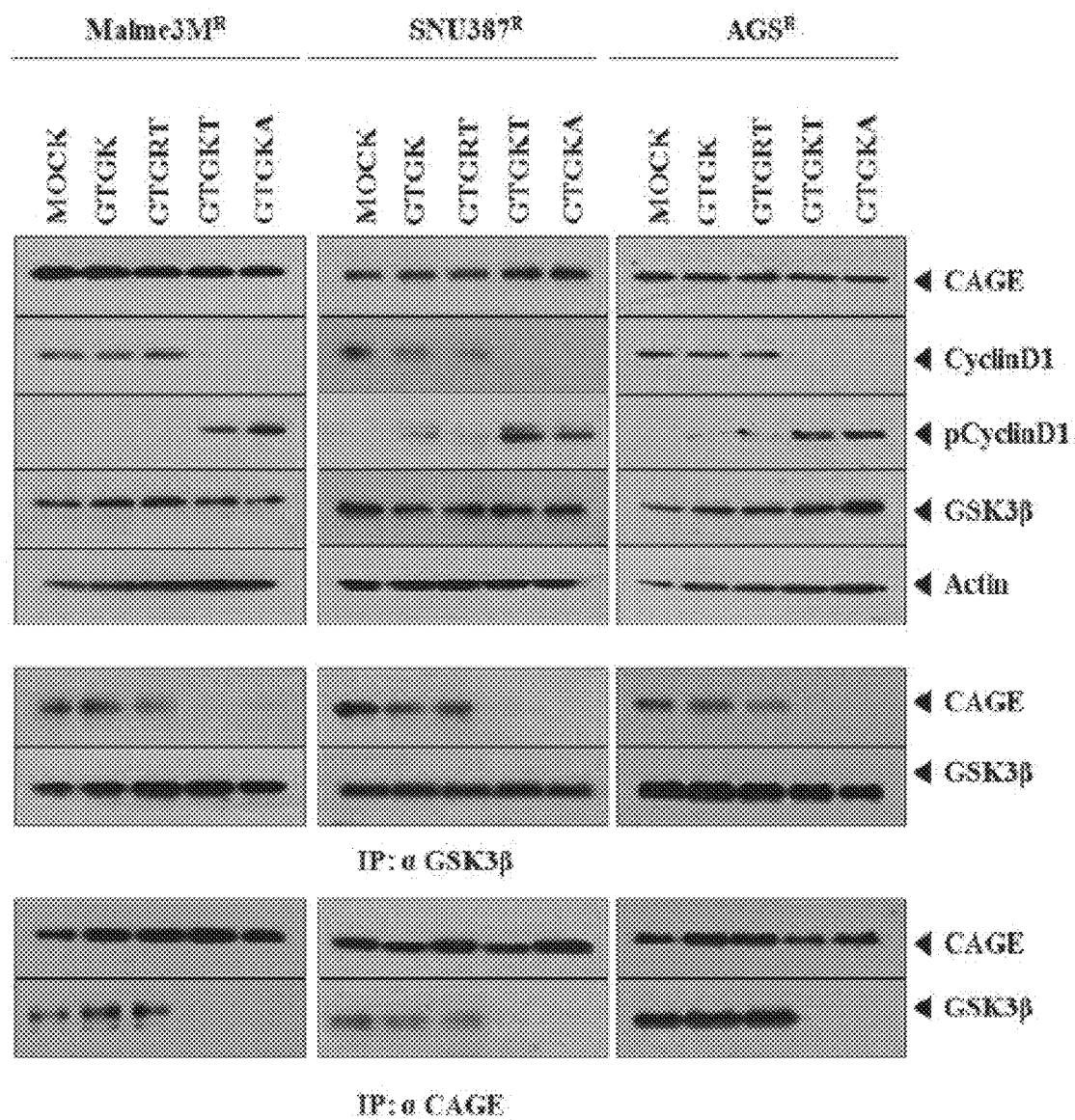
FIG. 5A shows a result of the same pattern with FIG. 4C in a celastrol-based anticancer drug-resistance melanoma cell strain.

After an inspection through the same manner with the GTGKT-based deletion and mutation peptides in celastrol-resistance cell strains Malme3M$^R$, SNU3SM$^R$, AGS$^R$) respective to melanoma, liver cancer, and gastric cancer, it could be seen from FIG. 5A that a GTGKT peptide and a GTGKA peptide suppress the inter-binding between CAGE and GSK3β proteins to control an expression level of Cyclin D1.

Figure 5B:
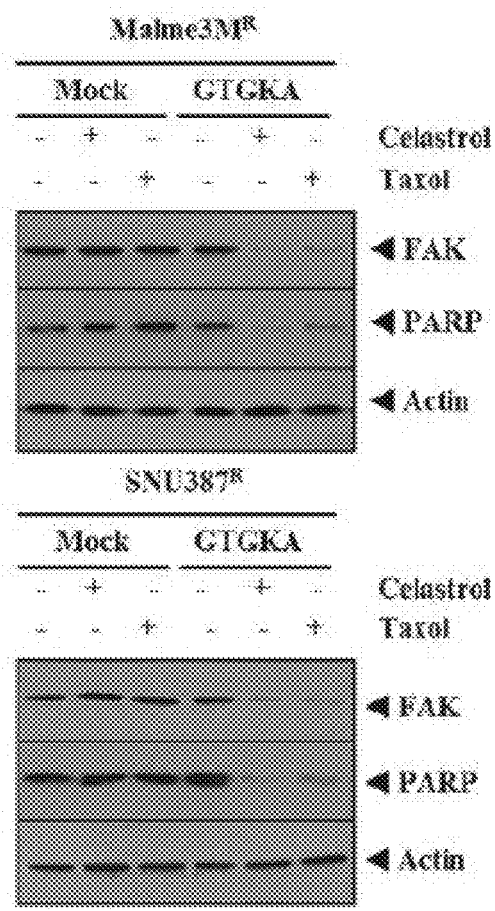
FIG. 5B shows a result of confirming anticancer activity of GTCKA in a celastrol-based anticancer drug-resistance melanoma cell strain through cleavage of PARP and PAK which are apoptotic factors.

Additionally, it was confirmed that a GTGKA peptide induced cell apoptosis against an anticancer drug in the cell strains (Malme3M$^R$, SNU38M$^R$) respective to melanoma and liver cancer (FIG. 5B).

Those results are summarized in FIG. 6.

<Suppression of Anticancer Drug-Resistance and Tumor Generation by GTGKT-Based Oligopeptide>

To confirm anticancer activity of a GTGKT-based oligopeptide, the MIT assay and the western blot according to a known method was performed using an immunodeficiency mouse. Then, it could be seen how the GKCKT-based oligopeptide affected tumor generation.

Figure 7A:
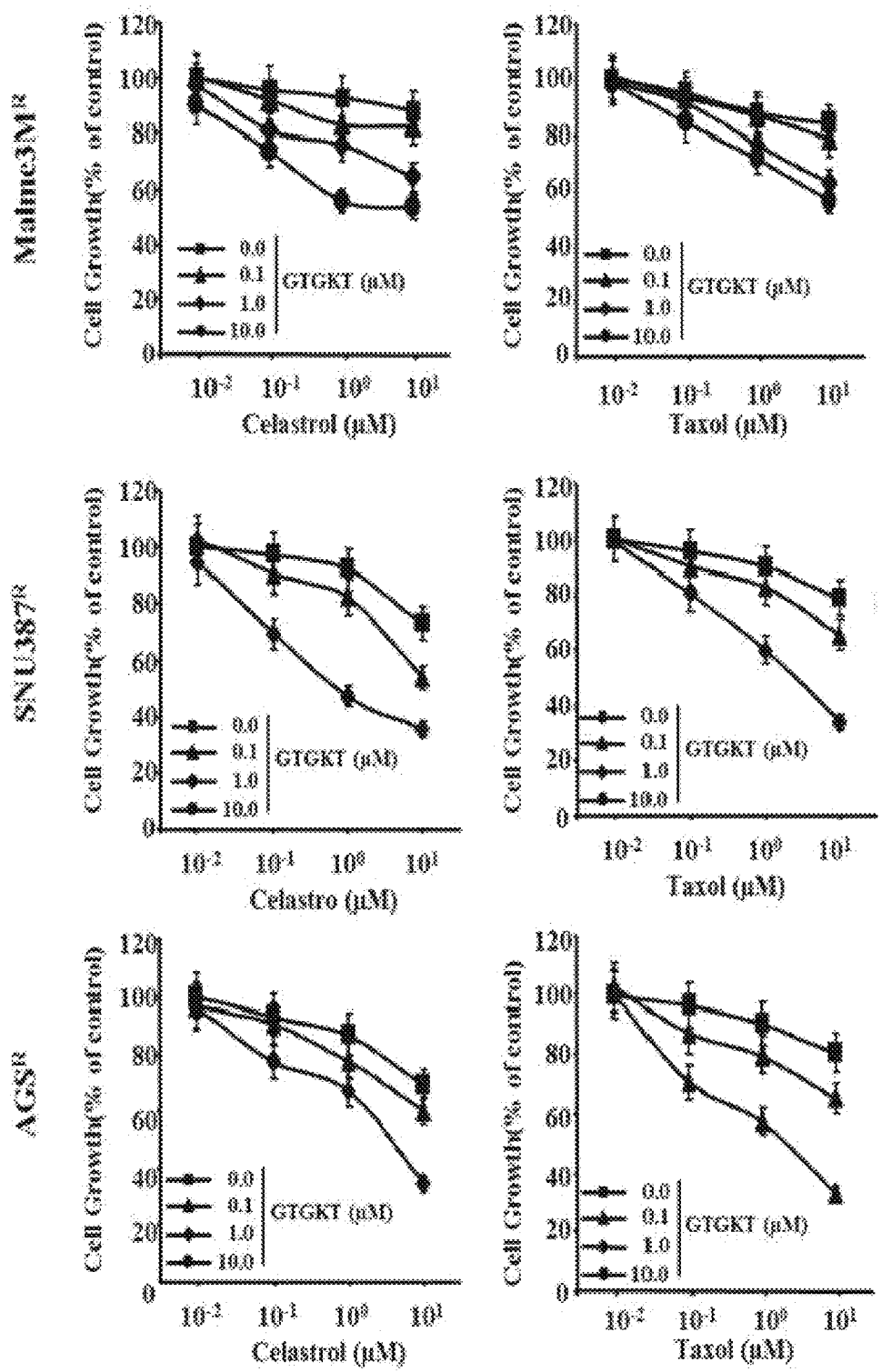
FIG. 7A shows a result of MTT assay that a GTGKT suppresses resistance against an anticancer drug in a celastrol-based anticancer drug-resistance cell strain.
Figure 7B:
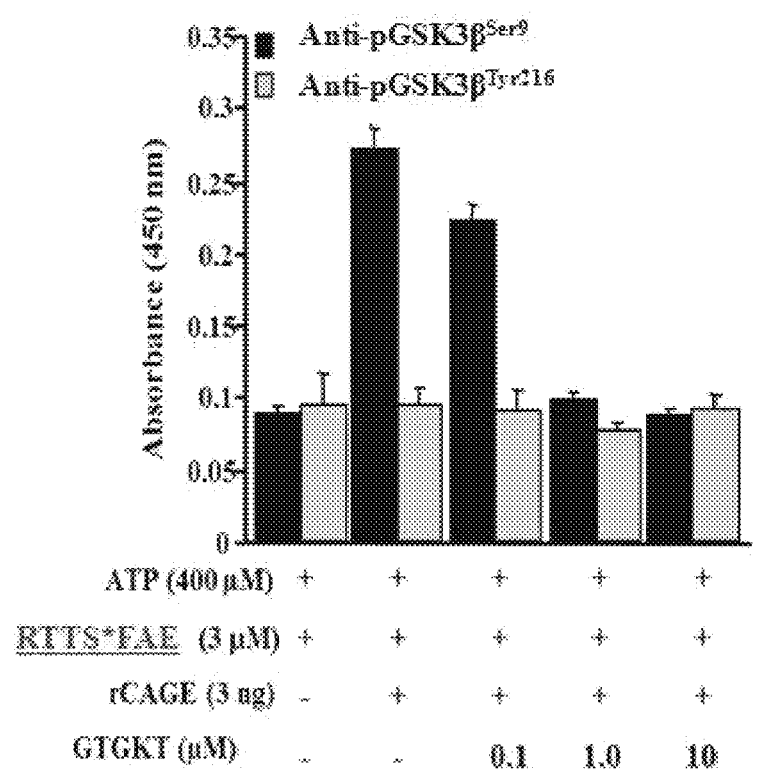
FIG. 7B shows a result of kinase assay that a CAGE protein specifically, phosphorylates GSK3β Ser9 residues and a GTGKT hinders the phosphorylation.

After transfecting a GTGKT peptide into melanoma, liver-cancer, and gastric-cancer cell strains (Malme3M$^R$, SNU38M$^R$, AGS$^R$) by concentration, anticancer drug resistance was inspected through the MTT assay. Then, as shown in FIG. 7A, I could be seen that the GTGKT peptide suppressed anticancer drug-resistance in each cell strain.

Figure 7C:
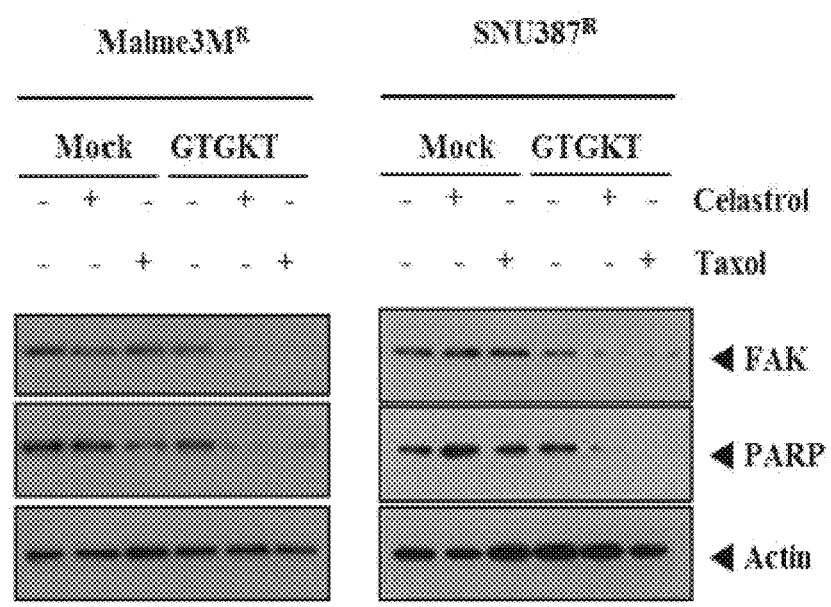
FIG. 7C shows a result of Western blot that the result of FIG. 7A is confirmed through cleavage of PARP and PAK which are apoptotic factors.

Additionally, it could be seen through the in vistro kinase assay that the GTCKT peptide suppressed phosphorylation of GSK3β Ser8 residues due to a reassociated CAGE protein and could be seen through the apoptosis inducing factors FAK and PARP cleavage that the GTGKT induced apoptosis against an anticancer drug (FIG. 7C).

Figure 8A:
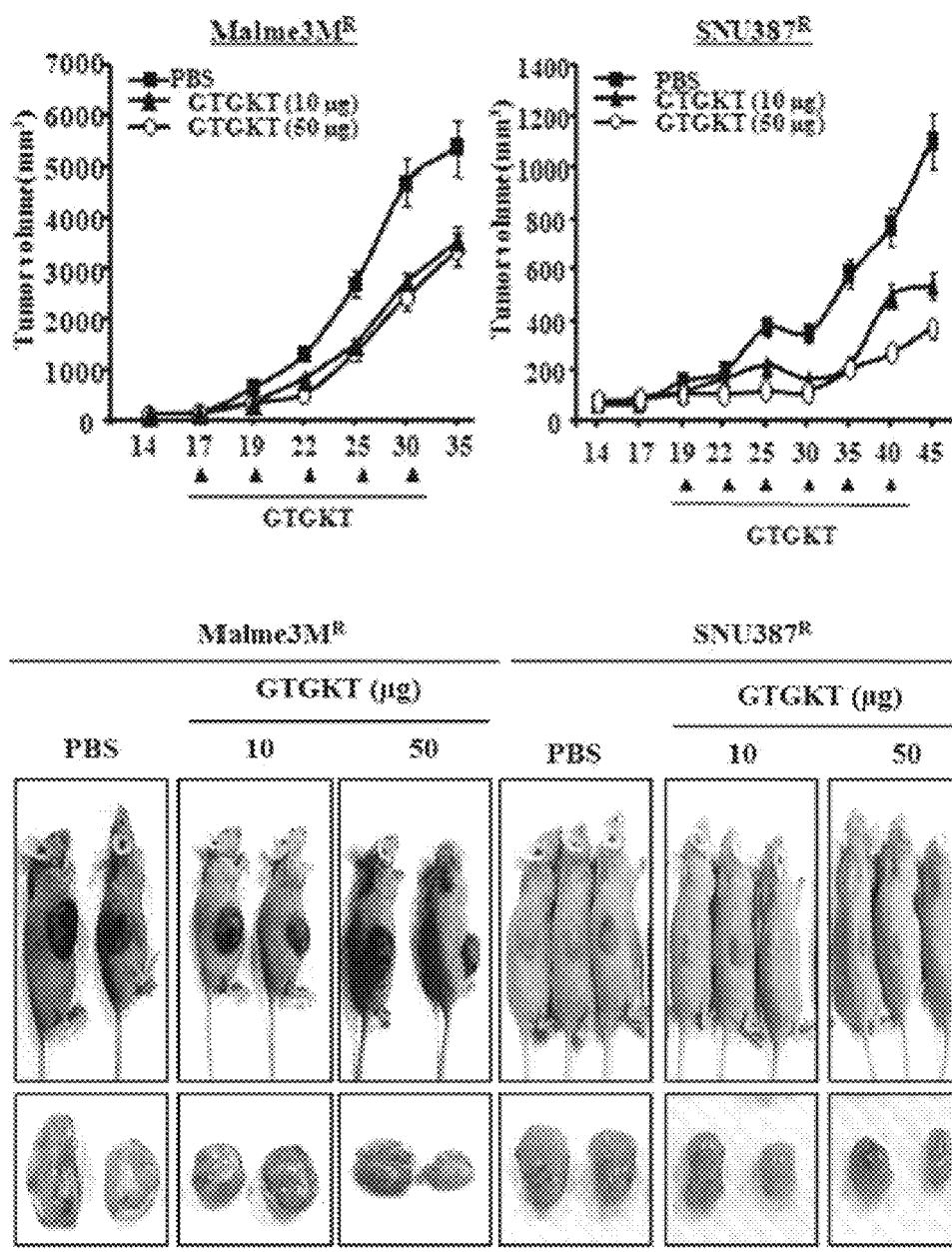
FIG. 8A shows a result that a GTGKT reduces a size of tumor, which is caused from a celastrol-based anticancer drug-resistance cell strain, in an immunodeficiency mouse.

To inspect an affection of GKGKT peptide to tumor generation, after injecting high-CAGE melanoma and liver-cancer cell strains (Malme3MR, SNU38R) into the side abdomen of an immunodeficiency mouse by a known method and then inducing a tumor, the GTGKT peptide was injected into a vein of the mouse's tail 5 times in total every 3 days for 2 weeks and a size variation of the tumor was examined. As a result, it could be seen from FIG. 8A that the GTGKT peptide reduced a size of the tumor due to the cancer cell strains.

Figure 8B:
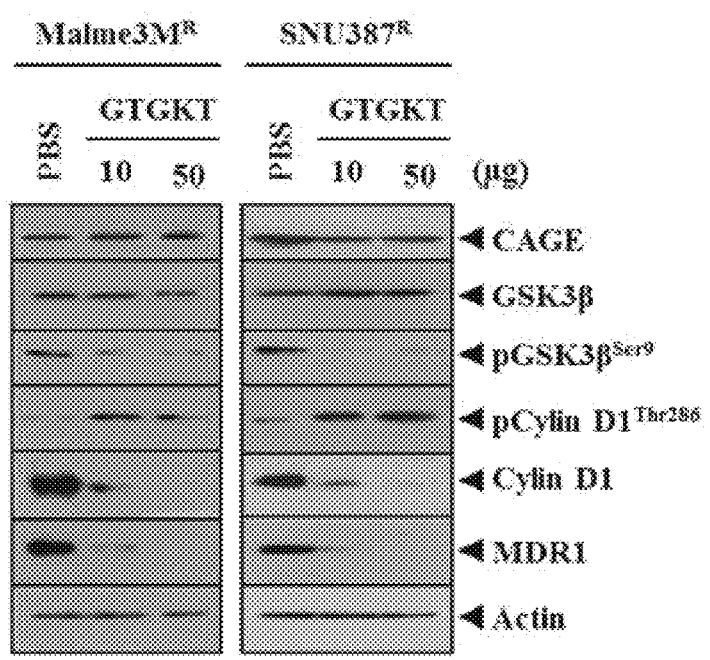
FIG. 8B shows a result of a gene expression pattern from a tumor tissue which has been used in the experiment of FIG. 8A.
Figure 8C:
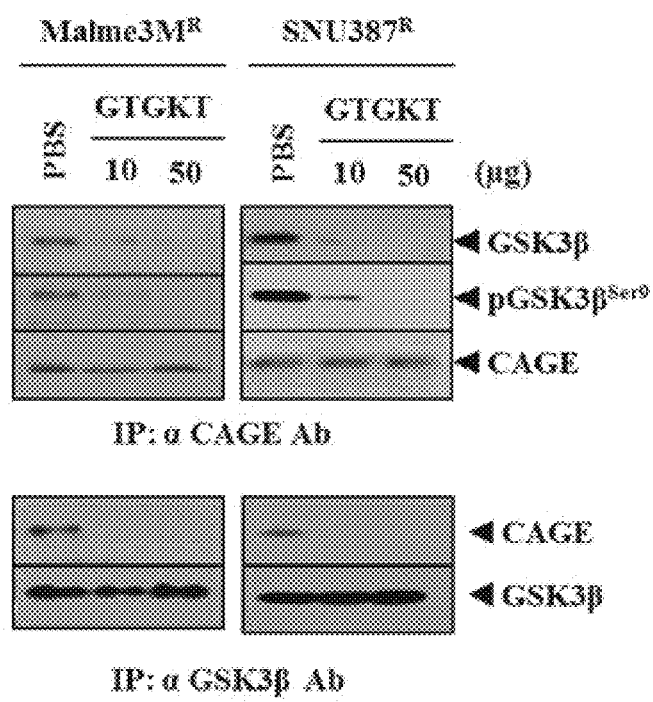
FIG. 8C shows a result that a GTGKT suppresses the inter-binding between a CAGE and a phosphorylated GSK3β from a tumor tissue which has been used in the experiment of FIG. 8A.

After finishing the experiment, a protein was collected from the tumor tissue through a known method, and then activity of protein expression and an inter-binding state were conformed through the Western blot and the immunoprecipitation. As a result, it could be seen from FIG. 8B that the GTGKT peptide suppressed the inter-binding between CAGE and GSK3β proteins to induce a decrease of protein expression of Cyclin D1 by dephosphorylation of the GSK3β Ser9 and phosphorylation of Cyclin D Thr286 residues and also reduced an expression of MDR1 which is an anticancer drug resistance gene.

Figure 9A:
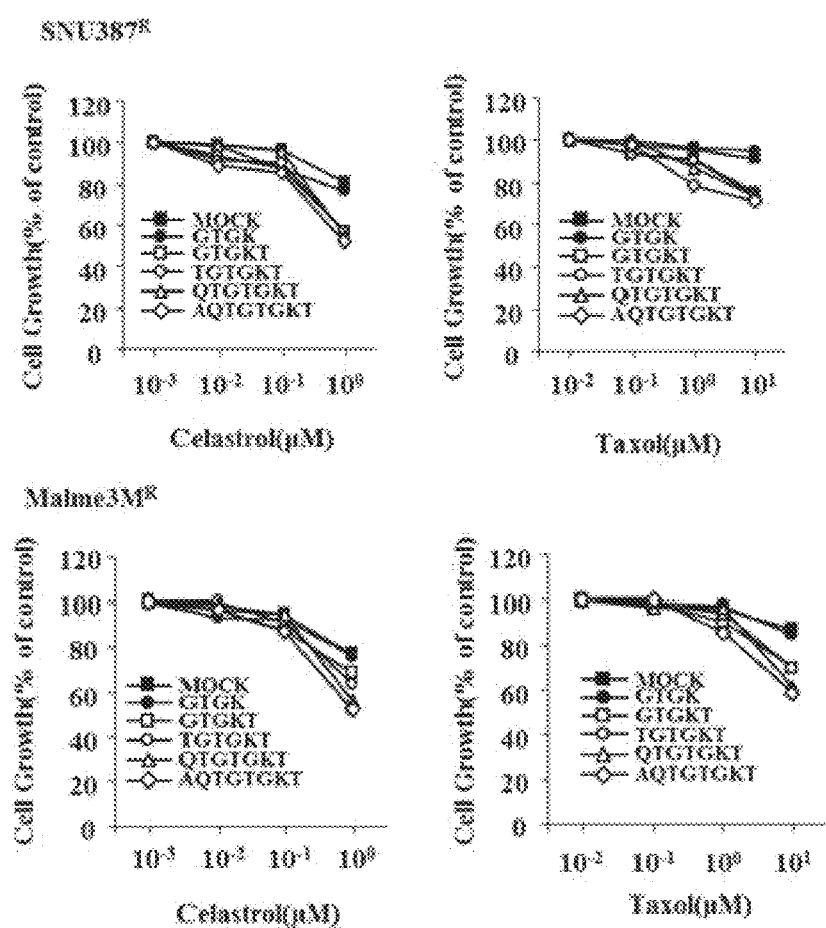
FIG. 9A shows a result of MTT assay that a GTGKT-based peptide affects anticancer drug resistance in a celastrol-based anticancer drug-resistance cell strain.

From an inspection of an anticancer drug-resistance state by the WIT assay for the purpose of confirming anticancer activity of a GTCKT peptide, it could be seen, as shown in FIG. 9A, that the GTGKT peptide suppressed anticancer drug resistance.

Figure 9B:
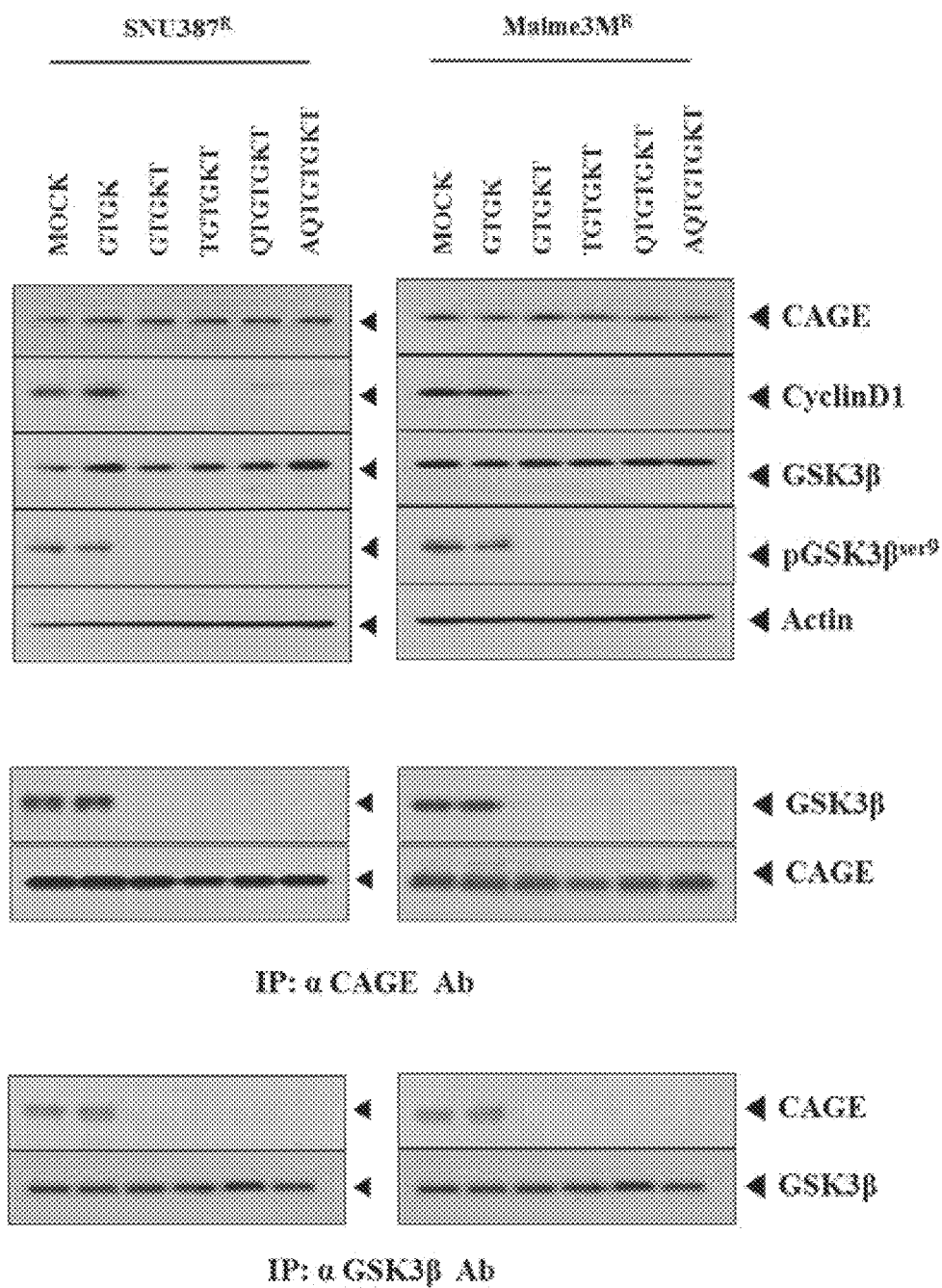
FIG. 9B shows a result that a GTGKT-based peptide affects phosphorylation of GSK3β Ser9 residues, accumulation of Cyclin D1 protein. and the inter-binding between CAGE and the phosphorylated GSK3β in a celastrol-based anticancer drug-resistance cell strain.

After treating a GTGKT peptide with high-CAGE melanoma and liver-cancer cell strains (Malme3M$^R$, SNU38$^R$), it could be seen from FIG. 9B that the GTGKT peptide suppressed dephosphorylation of GSK3 β Ser9 and expression of Cyclin D1 and hindered the inter-binding between CAGE and GSK3β proteins.

<Tumor Specificity of GTGKT-Based Oligopeptide>

To confirm whether a GTGKT-based oligopeptide with anticancer activity was a tumor-specific peptide, FITC-GTGKT was prepared to perform an inspection with an anticancer drug-resistance cell strain and an immunodeficiency mouse through a known method.

Figure 10A:
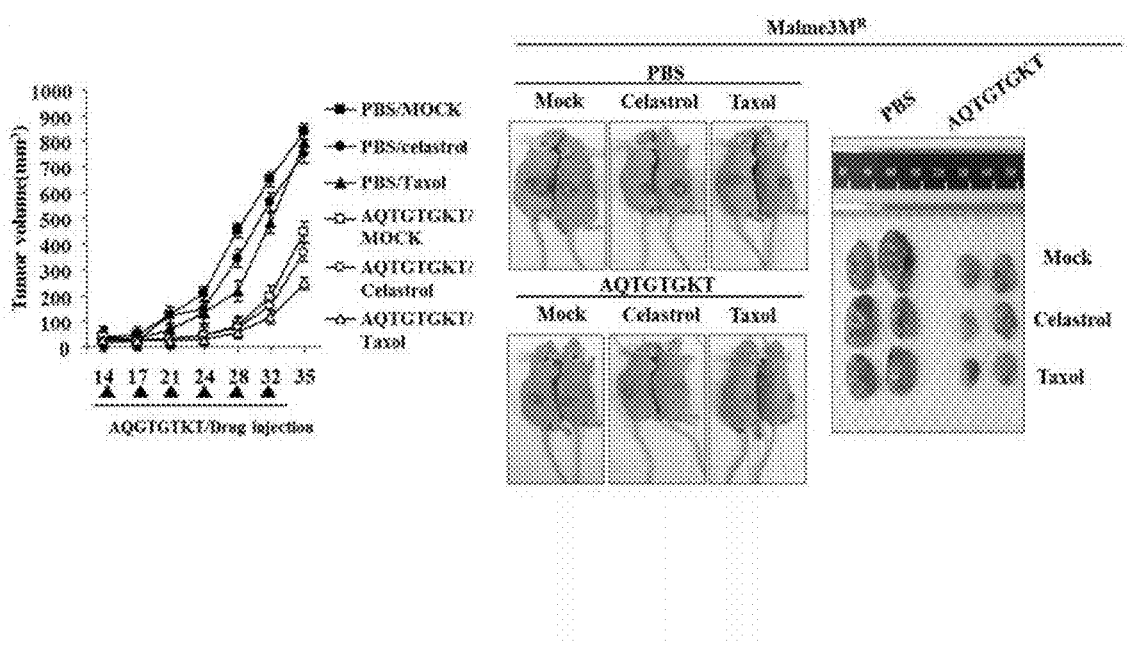
FIG. 10A shows a result of moving FITC-GTGKT, which is indicated by a fluorescent material, into a celastrol-based anticancer drug-resistance cell strain.

As a result of transfecting high-CAGE melanoma and liver-cancer cell strains (Malme3M$^R$, SNU38$^R$) and inspecting the state through a fluorescent microscope after 24 hours, it could be seen from FIG. 10A that the FITC-GTGKT migrated into the cells.

Figure 10B:
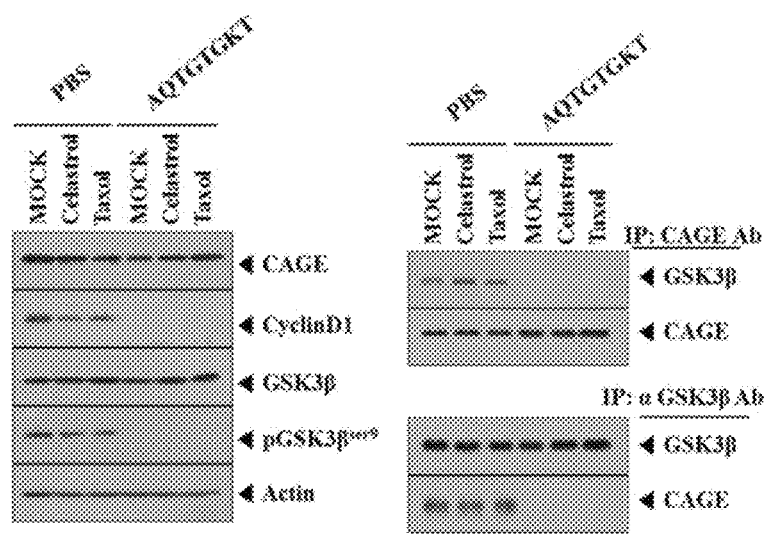
FIG. 10B shows a result of tumor-tissue specific infiltration of FITC-GTGKT.

After inducing a tumor from an immunodeficiency mouse through a known method and injecting FITC-GTGKT into a vein of the mouse's tail, normal tissues (brain, heart, spleen, liver, lung, etc.) and tumor tissues were extracted after 24 hours and then inspected using the small in vivo imaging system. As a result, it could be seen from FIG. 10B that the FIX-GTGKT specifically immigrated into the tumor tissues.

Additionally, it could be seen that a GTGKT peptide was bound specifically to a CAGE in the anticancer drug-resistance cell strains which had been used in the experiment.

While embodiments of the present disclosure have been shown and described with reference to the accompanying drawings thereof, it will be understood by those skilled in the art that various changes and modifications in form and details may be made therein without departing from the spirit and scope of the present disclosure as defined by the appended claims and their equivalents. For example, it may be allowable to achieve desired results although the embodiments of the present disclosure are preformed in other sequences different from the descriptions, and/or the elements, such as system, structure, device, circuit, and so on, are combined or assembled in other ways different from the descriptions, replaced or substituted with other elements or their equivalents.

Therefore, other implementations, other embodiments, and equivalents of the appended claims may be included in the scope of the appended claims.

What is claimed is:

1. A method of treating a drug-resistant cancer or tumor comprising administering to a subject in need thereof an oligopeptide consisting of the amino acid sequence of SEQ ID NO.1 (GTGKT) as an effective ingredient, wherein the cancer is a skin cancer, liver cancer, or gastric cancer.

2. The method of claim 1, wherein the oligopeptides kills a cancer cell resistant to celastrol or taxol.

3. A method of treating a drug-resistant cancer or tumor comprising administering to a subject in need thereof an oligopeptide consisting of the amino acid sequence of SEQ ID NO.2 (GTGKA) as an effective ingredient, wherein the cancer is a skin cancer, liver cancer, or gastric cancer.

4. The method of claim 3, wherein the oligopeptide kills a cancer cell resistant to celastrol or taxol.

* * * * *